United States Patent [19]

Hapstack et al.

[11] Patent Number: 5,285,689

[45] Date of Patent: Feb. 15, 1994

[54] PIPING INSPECTION INSTRUMENT CARRIAGE WITH PRECISE AND REPEATABLE POSITION CONTROL AND LOCATION DETERMINATION

[75] Inventors: Mark Hapstack, North Augusta, S.C.; Ted R. Talarek, Augusta; W. Thor Zollinger, Martinez, both of Ga.; Frank M. Heckendorn, II, Aiken; Larry R. Park, North Augusta, both of S.C.

[73] Assignee: The United States of America as represented by the United States Department of Energy, Washington, D.C.

[21] Appl. No.: 730,425

[22] Filed: Jul. 16, 1991

[51] Int. Cl.$^5$ .................... G01N 29/10; G01N 29/24
[52] U.S. Cl. ...................... 73/623; 324/220; 73/601
[58] Field of Search ............ 73/622, 623, 602, 619, 73/865.8, 601; 324/219, 220, 221

[56] References Cited

U.S. PATENT DOCUMENTS

| 4,162,635 | 7/1979 | Triplett et al. | 73/623 |
|---|---|---|---|
| 4,460,920 | 7/1984 | Weber et al. | 358/100 |
| 4,506,549 | 3/1985 | Thome | 73/582 |
| 4,560,931 | 12/1985 | Murakami et al. | 324/220 |
| 4,581,938 | 4/1986 | Wentzell | 73/623 |
| 4,621,532 | 11/1986 | Takagi et al. | 73/623 |
| 4,677,865 | 7/1987 | Lehmann | 73/866.5 |
| 4,722,001 | 1/1988 | Röhrich et al. | 324/220 |
| 4,769,598 | 9/1988 | Krieg et al. | 324/219 |
| 4,856,337 | 8/1989 | Metala et al. | 73/601 |
| 4,974,168 | 11/1990 | Marx | 73/622 |

FOREIGN PATENT DOCUMENTS 0231260  9/1988  Japan ..................... 73/622

Primary Examiner—Hezron E. Williams
Assistant Examiner—Rose M. Finley
Attorney, Agent, or Firm—Brian R. Tumm; Harold M. Dixon; William R. Moser

[57] ABSTRACT

An instrument carriage for inspection of piping comprises front and rear leg assemblies for engaging the interior of the piping and supporting and centering the carriage therein, and an instrumentation arm carried by a shaft system running from the front to rear leg assemblies. The shaft system has a screw shaft for moving the arm axially and a spline gear for moving the arm azimuthally. The arm has a pair of air cylinders that raise and lower a plate in the radial direction. On the plate are probes including an eddy current probe and an ultrasonic testing probe. The ultrasonic testing probe is capable of spinning 360° about its axis. The instrument carriage uses servo motors and pressurized air cylinders for precise actuation of instrument components and precise, repeatable actuation of position control mechanisms.

19 Claims, 4 Drawing Sheets

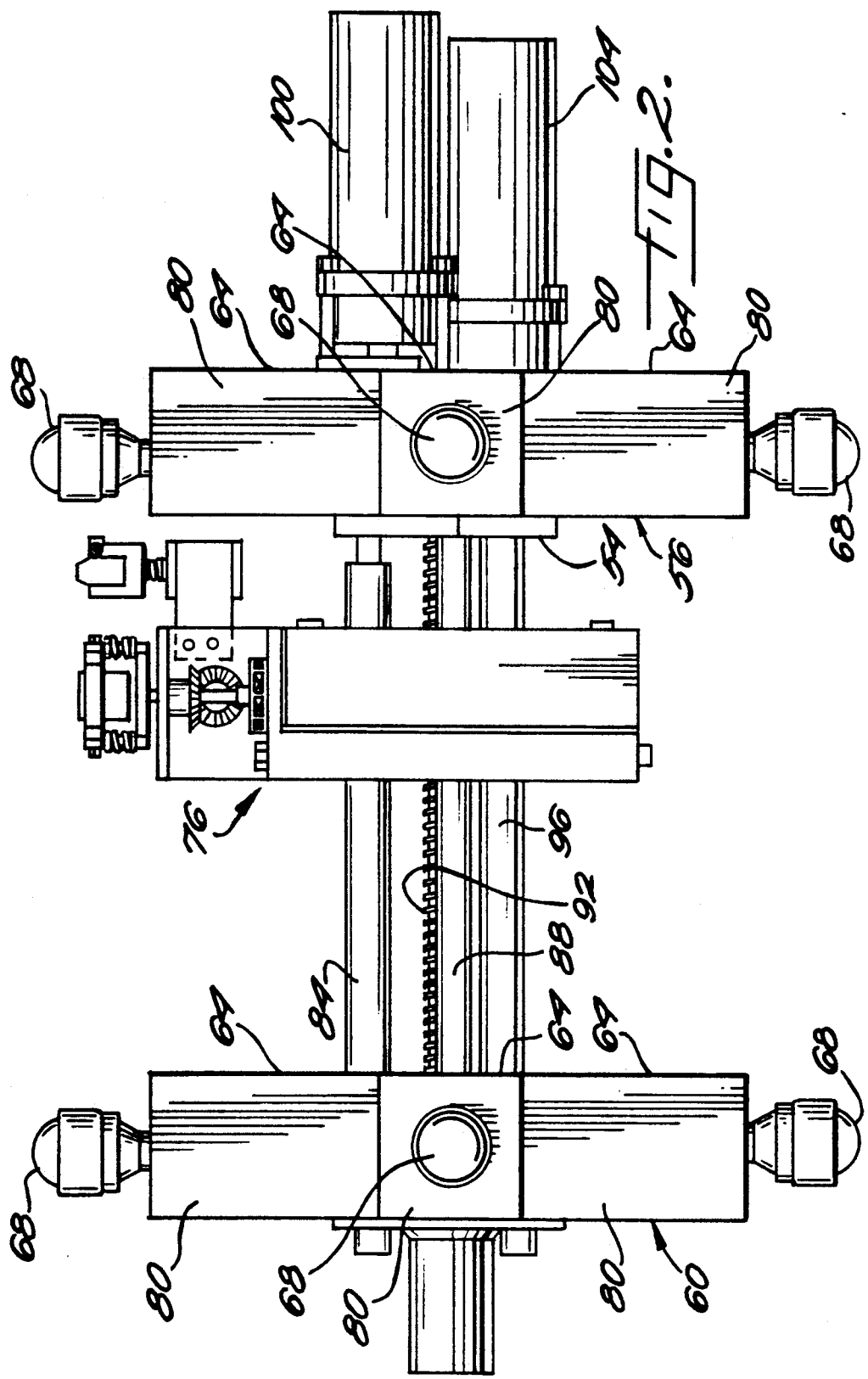

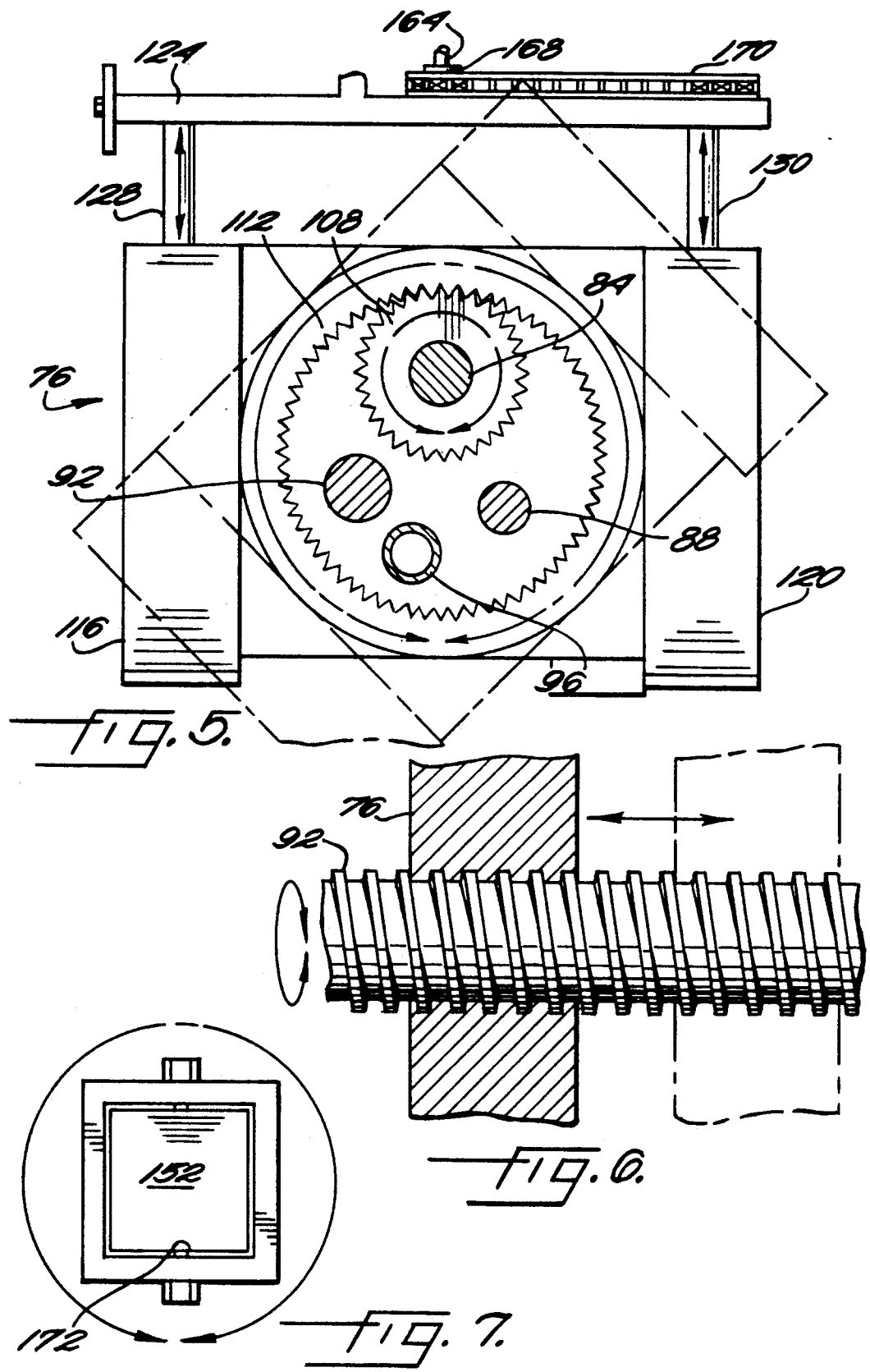

PIPING INSPECTION INSTRUMENT CARRIAGE WITH PRECISE AND REPEATABLE POSITION CONTROL AND LOCATION DETERMINATION

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to apparatus for inspecting the interior of piping. In particular the present invention relates to piping inspection, instrumentation-carrying apparatus having the capability of locating and scanning a specific feature along the interior of the piping.

2. Discussion of Background

Throughout industry, piping is used to convey fluids of every kind over short distances and long. Because of the adverse effects of stress, temperature, and fluids flowing through pipes, both the effects of specific fluids (corrosion) and the effects of fluid flow in pipes generally (erosion), the piping will eventually degrade and may fail completely or may cease to be serviceable or may simply begin to leak. Flaws frequently begin to form at welded joints. However, even newly welded pipe joints can also have flaws that will cause leaks or pipe failure.

The integrity of piping is an important industrial concern and can become crucial depending on a number of factors, including the volume of material transported by the piping per day, the hazardous nature of the material, the cost of the fluid transported, and the impact of a loss of the fluid on the user's operation at the fluid's destination.

Pipe inspection can prove very useful in avoiding pipe failure by determining the condition of piping and how that condition changes over time. Welds can be inspected visually, ultrasonically and using eddy currents. Not only is periodic pipe inspection useful during operation, but pipe inspection prior to use may be especially important. For example, it is prudent to conduct a pre-service inspection of piping that will carry hazardous or radioactive fluids to verify the condition of welds or to fix flaws before the interior of the piping becomes contaminated.

There are a number of piping inspection devices. Some of these are self-propelled and others are pulled or pushed by pipe crawlers or other means. See for example the pipe inspection devices described by Wentzell in U.S. Pat. No. 4,581,938, Takagi, et al. in U.S. Pat. No. 4,621,532 and Weber, et al. in U.S. Pat. No. 4,460,920. Pipe inspection can be done by ultrasonic transducers, eddy current sensors and visual devices. See Metala, et al. (U.S. Pat. No. 4,856,337), Krieg, et al. (U.S. Pat. No. 4,769,598) and Weber, et al. Weber includes a television camera with his pipe inspection device. Metala, et al. and Krieg, et al. carry both ultrasonic and eddy current measuring equipment. A companion application, commonly assigned, titled "Pipe Crawler With Extendable Legs", Ser. No. 679,497 filed Apr. 2, 1991, now U.S. Pat. No. 5,121,694 is incorporated by reference and describes a system for distribution of air via manifolds and solenoid switches. Also, see issued U.S. Pat. No. 5,018,451, commonly assigned, for a description of another pipe crawler such as could be used to move a pipe inspection apparatus.

Inspecting the interior of piping must be coupled with a fairly accurate system for knowing where the inspection device is and how it is oriented. Sometimes only distance in one direction is needed, distance that can be obtained from a simple odometer or from the length of the tether, for carrying power cables, air hoses, and the like, that trails from the inspection device to the entrance of the pipe. If the pipe has a number of bends and variations in diameter, and especially if the area to be inspected is relatively small, more precise locational information may be needed, sometimes, in fact, full coordinate information. The device as described by Thome in U.S. Pat. No. 4,506,549 provides position information in four dimensions: axial, radial, azimuthal and rotational about itself.

However, there remains a need for a pipe inspection device that is capable of making minute inspections and of knowing the precise location of the inspected areas for comparison to previously inspected areas. Fine inspections can enable pipe flaws and changes in those flaws to be detected, analyzed and corrected sooner rather than later.

SUMMARY OF THE INVENTION

According to its major aspects, the present invention is an instrument carriage for inspecting a feature on an interior surface of piping. The carriage has a frame carrying front and rear sets of radially extendable legs that engage the interior surface of the pipe and straddling the feature, means for finding the feature, and means for systematically scanning the feature and assoociating position information with the feature so that flaws, once found, can be located repeatedly with accuracy. The scanning means is an instrumentation arm that moves axially, radially and azimuthally and can, in a horizontal pipe, determine absolute orientation of the carriage. The arm moves along two mutually orthogonal coordinates, oscillating back and forth in an axial coordinate with respect to the pipe while moving steadily along an azimuthal coordinate. Probes for ultrasonic and eddy current testing are carried by the arm. A camera assists in finding the features but is not required. If so desired, the ultrasonic testing probe or the eddy current probe may be extended to the pipe wall to perform a quick scan and check to see if the desired feature is present. At least one television camera is carried by the arm for finding features on the interior surfaces of the piping.

An important feature of the present invention is the combination of position control mechanisms that permit accurate and repeatable axial, radial and azimuthal movement of the probes. Because of this combination, features that were found to have small cracks or signs of stress can be located on a second pass through the piping. Scanning results of more than one examination can be aligned within a few hundredths of an inch for analysis.

Another important feature of the present invention is the location of the instrumentation arm between the front and rear leg assemblies. This position requires the carriage leg assemblies to straddle the feature to be examined, resulting in improved stability for measurement. The importance of stability cannot be too strongly emphasized because of the need for fine measurements.

Another feature of the present invention is the method for scanning a feature. In particular, the center of a feature is located and scanned systematically along two mutually orthogonal coordinates. The arm oscillates in one direction while traversing in a second direction.

The stiffened, double air cylinders used for radial extension of the probes is another feature of the invention. It provides more stability for the plate that carries the probes than a single air cylinder.

The wire guide for carrying wiring and air hoses from one leg assembly to another and its location are another feature of the present invention. Since the instrumentation arm rotates at least 360 degrees azimuthally and engages the inside surface of the piping, the wire guide must be radially inside the arm and preferably carried by a part that does not rotate so that the wires do not become twisted. The wire guide is a hollow tube that runs from front to rear leg assembly, running axially and located radially within the ring gear that is rotated by a spline gear to rotate instrumentation arm. Thus the wiring and air hoses are protected and kept from fouling on the rotating and advancing instrumentation arm.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 2 is a side view of an instrumentation carriage according to a preferred embodiment of the present invention;

FIG. 5 is a detailed side view of the instrumentation carriage arm of FIG. 2 showing the azimuthal and radial movement of the arm;

FIG. 6 is a detailed side view of the instrumentation arm of FIG. 2 showing axial movement;

FIG. 7 is a top view of the ultrasonic detector of the instrumentation carriage arm of FIG. 2.

DETAILED DESCRIPTION OF A PREFERRED EMBODIMENT

Figure 1:
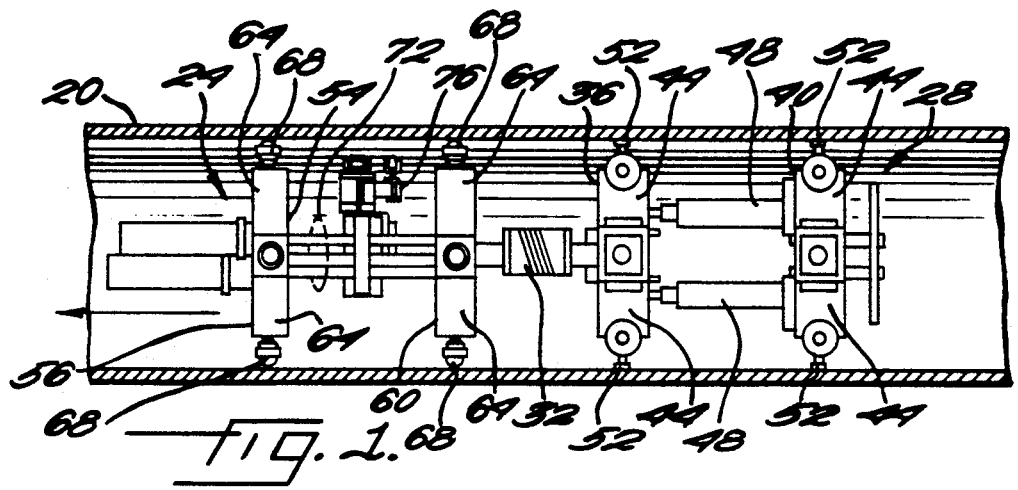
FIG. 1 is a partially cut-away view of a section of pipe with a pipe crawler pushing an instrumentation carriage according to a preferred embodiment of the present invention.

Referring now to FIG. 1, there is illustrated a section of piping 20 in cross section. Moving within piping 20 is a pipe inspection carriage 24, in accordance with a preferred embodiment of the present invention, being pushed by a pipe crawler 28. Pipe inspection carriage 24 is connected to pipe crawler 28 by a flexible coupling 32 that enables carriage 24 to be pushed through bends in piping 20. Flexible coupling 32 is preferably a cylinder with a spiral groove cut through it.

Pipe crawler 28, which is not part of the present invention can be any type capable of providing pushing or pulling power to carriage 24. Specifically, there are pipe crawlers that move in "inchworm" fashion, as in the case of crawler 28, with a front leg assembly 36 and a rear leg assembly 40 each having a plurality of leg cylinders 44. Front and rear leg assemblies 36 and 40 are connected by one or more air cylinders 48. Each leg cylinder has a foot 52 for frictionally engaging piping 20. The movement of crawler 28 is then achieved by the following sequence: leg cylinders 44 of rear leg assembly 40 radially extend feet 52 to engage the interior wall of piping 20; front leg assembly 36 is moved forward by air cylinders 48 along piping 20; then leg cylinders 44 of front leg assembly 36 extend feet 52 to engage the wall of piping 20; leg cylinders 44 of rear leg assembly 40 retract; and rear leg assembly 40 is pulled toward front leg assembly 36 by air cylinders 48. As crawler 28 moves forward, it pushes carriage 24.

Carriage 24 has a frame 54 to which is attached a front leg assembly 56 and a rear leg assembly 60. Front and rear leg assemblies 56, 60 are spaced apart and their spacing is rigidly maintained, as will be further described below. Each leg assembly has a plurality of leg cylinders 64 that extend radially to engage the interior surface of piping 20; each leg 64 has a ball transfer 68 or other wall-engaging device on the end thereof to facilitate low-frictional engagement and movement of carriage 24. Axial movement of carriage 24 through piping 20 is controlled by crawler 28. Front and rear leg assemblies 56, 60, by engaging the interior surface of piping 20, stabilize and center carriage 24 radially with respect to the axis of piping 20. Electrical wiring and air hoses for leg cylinders are not shown for simplification. A preferred method for delivery of air to air cylinders via manifolds and solenoid switches is described in a companion application titled Pipe Crawler With Extendable Legs, recently filed application Ser. No. 679,497, now U.S. Pat. No. 5,121,694, incorporated herein by reference.

Carriage 24 has shaft system 72 for, among other purposes, maintaining the spacing between front and rear leg assemblies 56, 60 of carriage 24. Shaft system 72 carries an instrumentation arm 76 for scanning features on the interior surface of piping 20 and at least one television camera (not shown on FIG. 1) for assistance in finding such features. Additional cameras may be used for viewing in the direction carriage 24 is moving.

FIG. 2 shows a side view of carriage 24. Front and rear leg assemblies 56, 60 operate by air cylinders 80 or other means such as hydraulic cylinders or electromechanical cylinders. Preferably at least three legs 64 and most preferably four legs 64, as shown in FIG. 2 (three of which are visible in the figure), all at right angles with respect to adjacent legs 64 are provided to center and support carriage 24 in piping. Each leg 64 has ball transfer 68 on its end that provides low-friction movement when the legs 64 of carriage 24 engage the interior surface of piping 20. Between front and rear leg assemblies 56, 60 are two splined shafts 84 and 88, deployed in parallel with each other and parallel to the axis of carriage 24. In addition to shafts 84 and 88, there is a ball screw shaft 92 and a wire tube 96 (see also FIG. 3). Tube 96 simply serves as a conduit for running wiring and air hoses from front leg assembly 56 to rear leg assembly 60, keeping the wiring and air hoses from being caught on instrumentation arm 76. Spline shaft 84 assists in the rotation of instrumentation arm 76 about the axis of carriage 24, as will be described below. Spine shaft 88 is used for guiding linear travel. It also provides stability, or rigidness, to the carriage acting as a third brace, along with spline shaft 84 and ball screw shaft 92.

At the rear of rear leg assembly 60 are two electrical motors. Motor 104 is for producing linear motion of instrumentation arm 76; motor 100 is for producing rotational, or azimuthal, motion of instrumentation arm 76. As motor 104 turns screw shaft 92, as illustrated in FIG. 6, instrumentation arm 76 is moved linearly in one direction or another depending on whether screw shaft is being turned clockwise or counter-clockwise.

Figure 3:
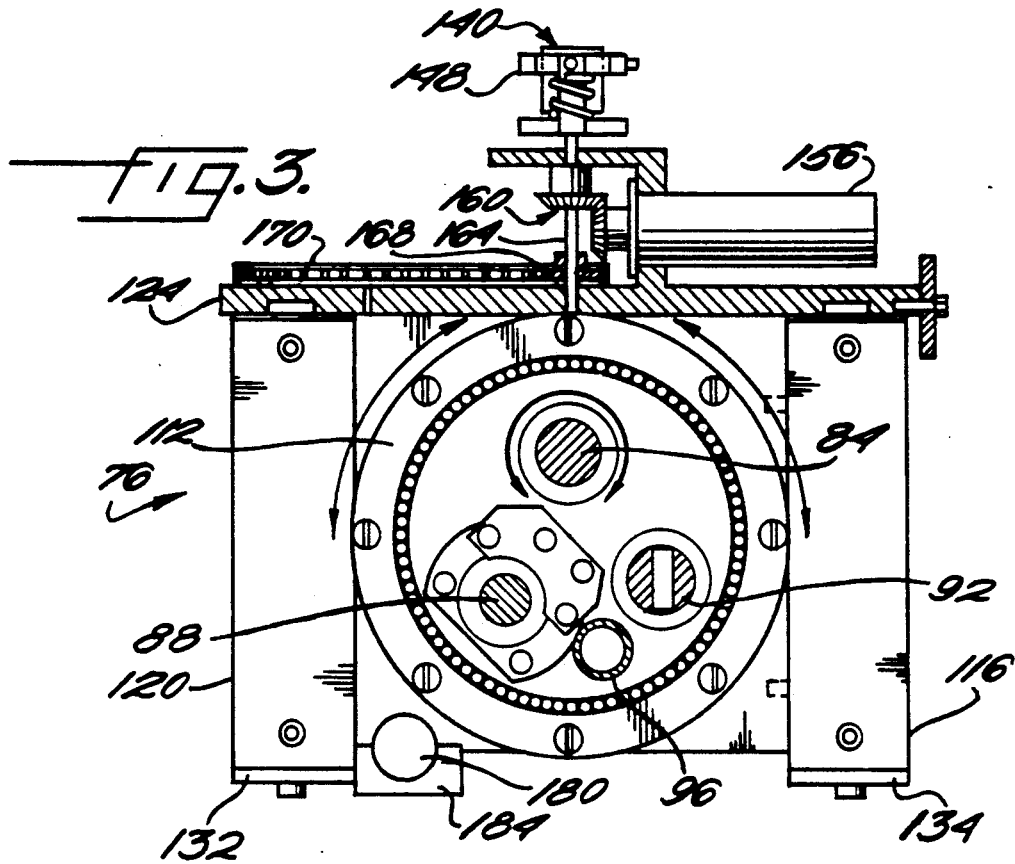
FIG. 3 is an end view of the arm of the instrumentation carriage of FIG. 2.
Figure 4:
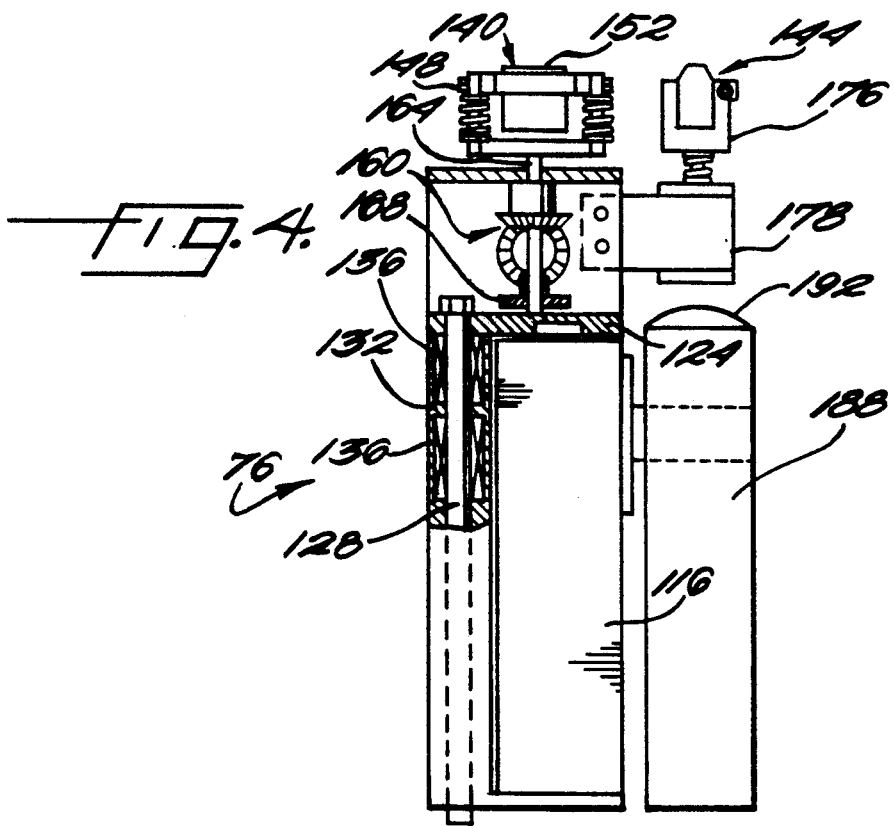
FIG. 4 is a side view of the instrumentation carriage arm shown in FIG. 3.

Motor 100 turns spline shaft 84 which, as best seen in FIGS. 3 and 5, turns gear 108 which drives ring gear 112 so that instrumentation arm 76 rotates, azimuthally, about the axis of carriage 24. In FIGS. 4 and 5, radial movement from the axis of carriage 24 outwardly to the interior surface of piping 20 is achieved through two air cylinders 116, 120 mounted in parallel and on opposing sides of instrumentation arm 76 that move instrumentation plate 124 radially in and out. Each air cylinder 116, 120 has a shaft 128, 130, respectively, for stiffening sliding motion in stiffening blocks 132, 134, respectively, that move in bearings 136 (FIG. 4).

Plate 124 carries an ultrasonic testing probe 140 and an eddy current probe 144. Ultrasonic probe 140 is mounted on a gimbal 148 so that the face 152 of probe 140 engages the interior surface of piping 20 fully regardless of the angle of approach. Probe 140 is rotated through one complete revolution by a motor 156 connected via miter gears 160 to a shaft 164 running through the center of probe 140. Control of the degree of revolution is imposed by a sprocket 168 also mounted to shaft 164 which sprocket rotates a chain 170 through a portion of its length. On face 152 of probe 140 is a small hole 172 (FIG. 7) through which a fluid may be dispensed onto face 152. The fluid serves as both a lubricant and dielectric for good ultrasonic measurements.

Eddy current probe 144 is mounted near but to the side of ultrasonic testing probe 140 on an eddy current mount 176 (FIG. 4) that is held to instrumentation arm 76 by a bracket 178.

Ultrasonic probe 140 is preferably of the type that produces both a 45° shear wave to look for intergranular stress corrosion cracking and a 90° "straight-through" wave for laminate flaws. Eddy current probe tests magnetic properties, looking for a change in those properties present due to welding or other instigators.

Also mounted to instrumentation arm 76 is a electronic level potentiometer 180 mounted in a bracket 184. Potentiometer 180 has a pendulum-like electronic contact that hangs "down" in response to gravity as long as carriage is in a generally horizontal pipe, to indicate the direction of "down" in any section of piping 20, that is, potentiometer 180 indicates a gravitational "down" for establishing an absolute orientation for referencing all other directions and orientations of pipe carriage 24. In a vertical pipe, only relative position is known.

Mounted to either front or rear leg assembly 56, 60 is at least one camera 188. A single camera 188, as shown will be directed to the interior surface of piping 20 and the end of instrumentation arm 76 so that it can help to find surface features and observe engagement of ultrasonic testing probe with the wall of piping 20. Preferably equipped with a wide angle lens 192, camera 188 can determine if pipe crawler 24 has moved to within range of a reature on the inside surface of piping 20 and can observe the scanning of the feature by instrumentation arm 76. If a second camera is included with pipe crawler 24, it would be aimed in the direction of carriage travel.

Figure 8:
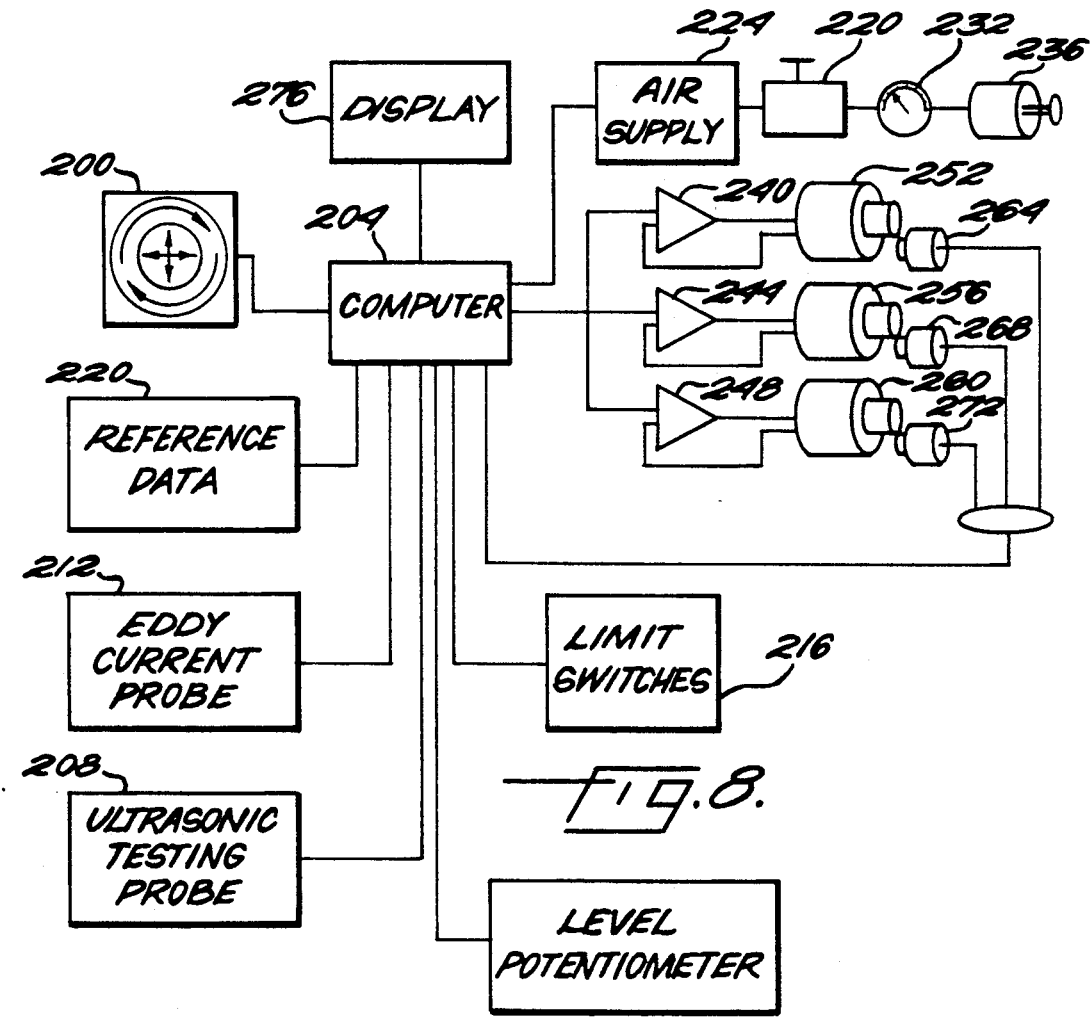
FIG. 8 is a schematic of the instrumentation carriage system according to a preferred embodiment of the present invention.

FIG. 8 is a schematic diagram of the control system of carriage 24. The device may be controlled with a joystick 200 or other manual or automatic device. The output of joystick 200 is input to a computer 204. Computer 204 receives data as input from ultrasonic testing probe 208 and eddy current probe 212 and limit switches 216 from the extreme axial, azimuthal, and spin movements of instrumentation arm 76. These are compared with reference inputs 200 to verify position information, as will be described in more detail below.

Computer 204 directs an air supply 224 that sends air through a regulator 228 and an air pressure gauge 232 to the air cylinders 236 of front and rear leg assemblies 56, 60 to control the extension of ball transfers 68 to engage the piping wall. Computer 204 also directs three servo amplifiers 240, 244, 248 that drive motors for linear motion 252, instrumentation arm rotational motion 256 and probe rotational motion 260. Each motor produces velocity feedback while potentiometers 264, 268 and 272, respectively, driven by motors 240, 244, 248, provide position feedback to computer 204. Ultrasonic testing probe 208, eddy current testing probe 212, limit switches 216, cylinders 236, motors 252, 256, 260, and potentiometers 264, 268, 272 are carried by instrumentation carriage 24. Joystick 200, computer 204, reference inputs 220, air supply 224, regulator 228, gauge 232, servo amplifiers 240, 244, 248, are remote from carriage 24 as is a display 276 of position information and the output of at least one on-board camera 280. These components are connected to carriage 24 by a tether.

In use, pipe crawler 28 pushes (or pulls) pipe carriage 24 along piping 20, ball transfers 68 in rolling engagement with piping 20 and camera 188 being trained on the inside surface of piping 20, until a surface feature such as a weld is found. Usually the length of the umbilical cord plus piping diagrams determines approximately where crawler 28 is in the piping system. Camera 188 is used to find the specific location of feature once the approximate location has been reached. Crawler 28 maneuvers carriage 24 so that carriage 24 straddles the feature, front leg assembly 56 on one side and rear leg assembly 60 on the other side of the feature. The arm is then extended radially and moves in the axial direction as the eddy current probe or ultrasonic testing probe is used to determine the center of the weld. Scanning the heat-affected-zone (HAZ) about a weld is done to look for signs of stress corrosion cracking and or other defects. Routinely every few years or so, piping is inspected. A crack that might be just forming is checked in the next inspection. Because of the importance of finding the same crack in two or more successive inspections several years apart, reliable position information, confirmed to some extent with visual correlation, is essential in any inspection program.

Instrumentation arm 76 extends ultrasonic testing probe 140 via air cylinders 132 and 140 to engage wall surface in the proximity of the surface feature. If the pipe has axial and circumferential welds, then the centerpoint of the intersection is found by the same process. The centerpoint of a weld can be found to within a few hundredths of an inch. Then rotating instrumentation arm 76 azimuthally, arm 76 moves back and forth axially by the alternate clockwise, counterclockwise turning of ball screw 92, to systematically scan the feature along two mutually orthogonal coordinates, in a circumferential weld, by oscillating in the axial direction and traversing in the azimuthal direction and producing outputs that reflect the results of the probes' measurements. Scanning is done with ultrasonic testing probe 140 and eddy current probe 144. Ultrasonic testing probe 140 rotates about its own axis. Position information regarding axial, radial, azimuthal locations is fed back to computer 204 so that the position of any flaw or crack in the feature can be established and located on a second trip into piping 20. Detailed visual inspection is by the television camera mounted on the arm. Any ultrasonic or eddy current image taken in a scan is aligned with an image from one or more previous scans.

Clearly, instruments other than eddy current probes and ultrasonic detectors could be carried by carriage 24 when needed to be brought to a particular location. For example, gripping devices can be carried for retrieval of objects or placement of sources for radiography; water nozzles and steam hoses, materials for coating and grinding tools can also be carried to a location for operating on the inside surfaces of piping.

It will be apparent to those skilled in the art that many changes and substitutions can be made to the preferred embodiment herein described without departing from the spirit and scope of the present invention which is defined by the appended claims.

What is claimed is:

1. An apparatus for inspecting a feature on an interior surface of piping, said apparatus comprising:
   a frame having a first end and a second end;
   a front leg assembly attached to said first end;
   a rear leg assembly attached to said second end,
   said front leg assembly having a first plurality of radially extendible legs and said rear leg assembly having a second plurality of radially extendible legs,
   said first and said second pluralities of radially extendible legs extending radially to engage said interior surface of said piping, said legs centering and supporting said apparatus;
   a first television camera mounted on said frame and directed toward said interior surface of said piping;
   means for systematically scanning said feature along three mutually orthogonal coordinates, said scanning means carried by said frame between said front and said rear leg assemblies and producing an output, said scanning means further comprising
   at least one probe,
   an instrumentation arm carrying said at least one probe,
   means carried by said frame for shifting said instrumentation arm axially in either direction,
   means carried by said frame for rotating said instrumentation arm azimuthally at least 360°, and
   means carried by said instrumentation arm for extending said at least one probe radially, said extending means having a plate carrying said at least one probe and a pair of air cylinders extending said plate radially, each of said pair of air cylinders positioned on either side of said instrumentation arm.

2. The apparatus as recited in claim 1, wherein said at least one probe is an ultrasonic probe; and said scanning means further comprises means for spinning said ultrasonic probe.

3. The apparatus as recited in claim 2, wherein said ultrasonic probe generates a shear wave and a straight-through wave.

4. The apparatus as recited in claim 1, further comprising means for analyzing said output, said analyzing means having means for storing reference data and means for receiving said output and aligning said output with reference data so that any differences between said output and said reference data can be seen.

5. The apparatus as recited in claim 1, wherein said instrumentation arm has a threaded hole and said shifting means further comprises a ball screw running axially through said threaded hole of said instrumentation arm.

6. The apparatus as recited in claim 1, wherein said apparatus further comprises a conduit between said front and back leg assemblies for carrying wires and air hoses.

7. An apparatus for inspecting a feature on an interior surface of piping, said apparatus comprising:
   a frame;
   means carried by said frame for engaging said interior surface of said piping and moving said apparatus through said piping, said engaging means centering and supporting said apparatus;
   means carried by said frame for systematically scanning said feature, said scanning means having
   at least one probe that produces an output responsive to said feature,
   an instrumentation arm,
   a plate attached to said arm, said plate carrying said at least one probe,
   means for extending said plate radially from said instrumentation arm,
   means carried by said frame for shifting said instrumentation arm axially, and
   means carried by said frame for rotating said instrumentation arm azimuthally at least 360°.
   said extending means, said shifting means, and said rotating means each generating position information associated by said scanning means with said output of said at least one probe.

8. The apparatus as recited in claim 7, wherein said at least one probe is an ultrasonic probe and an eddy current probe.

9. The apparatus as recited in claim 7, wherein said at least one probe is an ultrasonic probe that generates a shear wave and a straight-through wave.

10. The apparatus as recited in claim 7, further comprising means for analyzing said output, said analyzing means having means for storing reference data and means for receiving said output and aligning said output with reference data so that any differences between said output and said reference data can be seen.

11. The apparatus as recited in claim 7, further comprising means carried by said frame for determining the absolute orientation of said apparatus in horizontal piping.

12. The apparatus as recited in claim 7, further comprising an electronic level carried by said frame for determining the absolute orientation of said apparatus in horizontal piping.

13. An apparatus for inspecting a feature on an interior surface of piping, said apparatus comprising:
   a frame having a first end and a second end;
   a front leg assembly attached to said first end;
   a rear leg assembly attached to said second end,
   said front leg assembly having a first plurality of radially extendible legs and said rear leg assembly having a second plurality of radially extendible legs, said first and said second pluralities of radially extendible legs extending radially to engage said interior surface of said piping, said legs centering and supporting said apparatus;

means carried by said frame for systematically scanning said feature, said scanning means having at least one probe that produces an output responsive to said feature, an instrumentation arm, a plate attached to said arm, said plate carrying said at least one probe, means for extending said plate radially from said instrumentation arm, means carried by said frame for shifting said instrumentation arm axially, and means carried by said frame for rotating said instrumentation arm azimuthally at least 360°.

said extending means, said shifting means, and said rotating means each generating position information associated by said scanning means with said output of said at least one probe.

14. The apparatus as recited in claim 13, further comprising means for analyzing said output, said analyzing means having means for storing reference data and means for receiving said output and aligning said output with reference data so that any differences between said output and said reference data can be seen.

15. The apparatus as recited in claim 13, wherein said apparatus further comprises a conduit between said front and back leg assemblies for carrying wires and air hoses.

16. The apparatus as recited in claim 13, further comprising means for determining an absolute orientation of said apparatus in horizontal piping.

17. The apparatus as recited in claim 13, further comprising an electronic level for determining an absolute orientation of said apparatus in horizontal piping.

18. The apparatus as recited in claim 13, wherein said at least one probe further comprises an ultrasonic probe and an eddy current probe.

19. The apparatus as recited in claim 13, further comprising a television camera mounted on said frame and directed toward said interior surface of said piping.

* * * * *